(12) United States Patent
Kannajosyula et al.

(10) Patent No.: US 10,502,715 B2
(45) Date of Patent: Dec. 10, 2019

(54) SYSTEMS AND METHODS FOR SPECIMEN INSPECTION USING ULTRASONIC WAVE GENERATION

(71) Applicant: Quest Integrated, LLC, Kent, WA (US)

(72) Inventors: Haraprasad Kannajosyula, Seattle, WA (US); Phillip D. Bondurant, Covington, WA (US); Ali Minachi, Kent, WA (US)

(73) Assignee: Quest Integrated, LLC, Kent, WA (US)

( * ) Notice: Subject to any disclaimer, the term of this patent is extended or adjusted under 35 U.S.C. 154(b) by 230 days.

(21) Appl. No.: 15/793,837

(22) Filed: Oct. 25, 2017

(65) Prior Publication Data

US 2018/0128784 A1    May 10, 2018

Related U.S. Application Data

(60) Provisional application No. 62/412,569, filed on Oct. 25, 2016.

(51) Int. Cl.
*G01N 29/04* (2006.01)
*G01N 29/24* (2006.01)
(Continued)

(52) U.S. Cl.
CPC .......... *G01N 29/262* (2013.01); *G01N 29/04* (2013.01); *G01N 29/043* (2013.01); *G01N 29/24* (2013.01);
(Continued)

(58) Field of Classification Search
CPC ............. G01N 29/2412; G01N 29/348; G01N 29/262; G01N 29/043; G01N 29/2437; G01N 29/4463; G01N 2291/106
(Continued)

(56) References Cited

U.S. PATENT DOCUMENTS

| 6,434,539 B1 * | 8/2002 | Woodsum ................ H01Q 3/26 342/373 |
| 2003/0018261 A1 * | 1/2003 | Bae ..................... G01S 7/52025 600/447 |

(Continued)

FOREIGN PATENT DOCUMENTS

WO    2017/136692 A1    8/2017

OTHER PUBLICATIONS

Zhu, W., and J.L. Rose, "Lamb Wave Generation and Reception With Time-Delay Periodic Linear Arrays: A BEM Simulation and Experimental Study," IEEE Transactions on Ultrasonics, Ferroelectrics, and Frequency Control 46(3):654-664, May 1999.

*Primary Examiner* — Jacques M Saint Surin
(74) *Attorney, Agent, or Firm* — Christensen O'Connor Johnson Kindness PLLC

(57) ABSTRACT

Systems and methods for specimen inspection using ultrasonic wave generation are disclosed herein. In one embodiment, an apparatus for inspecting a solid object using ultrasound includes: a pulser having pulser ports for outputting electrical signals. The apparatus also includes a switching array for receiving the signals from the pulser ports as individual channels, and routing the signals to individual elements of a transmitter array. The apparatus also includes the transmitter array, where each element of the transmitter array generates ultrasound in the solid object in response to the signal received from the switching array.

27 Claims, 15 Drawing Sheets

(51) Int. Cl.
*G01N 29/44* (2006.01)
*G01N 29/34* (2006.01)
*G01N 29/26* (2006.01)

(52) U.S. Cl.
CPC ..... *G01N 29/2412* (2013.01); *G01N 29/2437* (2013.01); *G01N 29/34* (2013.01); *G01N 29/348* (2013.01); *G01N 29/44* (2013.01); *G01N 29/4463* (2013.01); *G01N 2291/106* (2013.01)

(58) Field of Classification Search
USPC .......................................................... 73/628
See application file for complete search history.

(56) References Cited

U.S. PATENT DOCUMENTS

| | | | |
|---|---|---|---|
| 2007/0240512 A1* | 10/2007 | Takada | G01N 29/041 73/588 |
| 2009/0048789 A1 | 2/2009 | Yu et al. | |
| 2011/0319767 A1* | 12/2011 | Tsuruno | A61B 8/04 600/459 |
| 2015/0260691 A1* | 9/2015 | Nakayama | G01N 29/2481 73/661 |

* cited by examiner

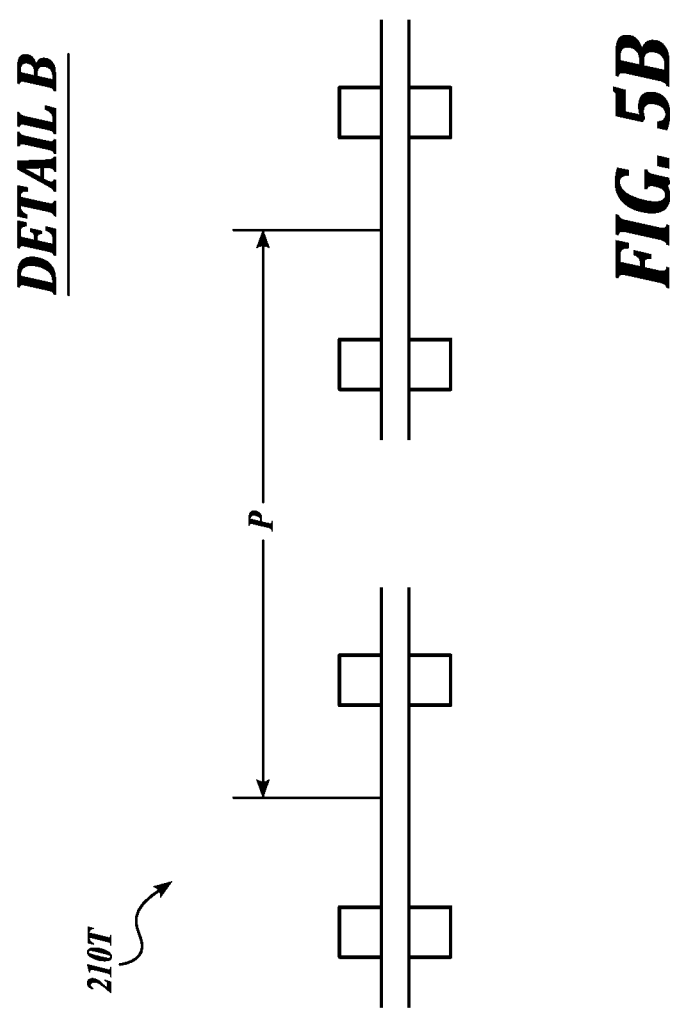

SYSTEMS AND METHODS FOR SPECIMEN INSPECTION USING ULTRASONIC WAVE GENERATION

CROSS-REFERENCE TO RELATED APPLICATION

This application claims the benefit of U.S. Provisional Application No. 62/412,569, filed Oct. 25, 2016, which is incorporated herein by reference in its entirety.

STATEMENT OF GOVERNMENT LICENSE RIGHTS

This invention was made with Government support under contract No. NNX16CL48P awarded by the National Aeronautics and Space Administration Shared Services Center. The Government has certain rights in the invention.

BACKGROUND

Metal pipes and plates are prone to cracks, corrosion and other material defects. Typically, cracks develop as relatively shallow defects caused by, for example, material fatigue or crystal defects. Over time, cracks become longer and deeper, and, given enough time, cracks may compromise the structural integrity of the pipe/plate. Therefore, metal parts are from time to time inspected to detect the presence and severity of crack. Additionally, layered composite materials may have flaws such as delamination (lack of adhesion between the layers). Some inspection technologies use ultrasonic waves to inspect for thesuch flaws.

FIG. 1 is a schematic view of defect detection in accordance with prior art. Some conventional technologies use piezoelectric transducers or electromagnetic acoustic transducers (EMAT) to generate ultrasonic waves in a solid material 6 (e.g., a metal plate). The conventional piezoelectric transducer includes a crystal 2 (e.g., a piezoelectric element) and a couplant 4 (e.g., gel or fluid) that transfers vibrations onto the solid material 6 (e.g., a steel plate). With another conventional technology, the EMAT 15 produces vibrations in a conductive and/or paramagnetic solid material 6. The EMAT 15 includes a permanent magnet 10 coupled with a coil 12. When the alternating current (AC) flows into the coil 12, magnetic field of the permanent magnet 10 interacts with magnetic field created by the AC current in the coil 12 to generate eddy currents in the solid material 6. The energy of these eddy currents are transferred to the crystal lattice of the solid material, producing ultrasonic waves.

When the ultrasonic waves reach a crack or flaw 5, reflected ultrasonic waves are generated. These reflected waves can be detected by a receiver that is also a piezoelectric element or an EMAT receiver. For example, at the receiving EMAT (not shown), the interaction of the reflected ultrasonic waves with the magnetic field of the receiving EMAT induces electrical currents in the receiving EMAT coil circuit. These induced currents can be measured, and further analyzed to characterize the crack 5.

The ultrasonic waves can be broadly classified into two categories: bulk waves and guided waves. Bulk waves, as the name suggests, can be generated into the bulk of the material at very high frequencies. Guided waves propagate at lower frequencies when compared to bulk waves for a given wall-thickness. Guided waves are characterized by multimodality, which is further characterized by the propagation of multiple packets of waves at distinct velocities for a given band of frequencies, each of which may be identified as a guided wave mode. Guided waves are typically employed in long distance inspection of structures. When applied to ultrasonic non-destructive inspection or testing of structures, the multimodality of guided waves can cause the corresponding signals to be unreadable or difficult to interpret.

FIG. 2 is a partially schematic, isometric view of defect detection in pipes using EMATs in accordance with prior art. Illustrated defect detection system 50 includes several EMAT transmitters (TX-es) 15-T interspersed with several EMAT receivers (RX-es) 15-R. These EMAT transmitters/receivers are distributed over the inner surface of a pipe 1. The individual EMAT transmitters 15-T generate ultrasound waves 40-F and 40-B in the material of the pipe 1 (i.e., the ultrasound waves guided in the forward and backward direction about the circumference of the pipe), as explained with reference to FIG. 1. When the ultrasound waves encounter the crack (defect) 5, the reflected ultrasound waves are generated and detected by one or more EMAT receivers 15-R. A distance from the EMAT receiver 15-R to the crack can be calculated based on the known time difference between the time when the ultrasound waves were transmitted by an EMAT transmitter 15-T and the time when the reflected ultrasound waves were received by an EMAT receiver 15-R. Therefore, the illustrated system emits guided waves about the circumference of the pipe 1. In other conventional technologies, the piezoelectric transmitters/receivers (collectively, transceivers or TRX-es) are used instead of the EMATs.

FIG. 3 is a schematic view of an EMAT 15 with multiple coils in accordance with prior art. The illustrated EMAT 15 uses multiple coils 12-1 to 12-4 that are overlaid and displaced as an array. Collectively, the multiple coils represent a coil transducer 22 of the EMAT 15. When the coils 12-1 to 12-4 are individually driven with phase-delayed ultrasonic pulsers, the combined ultrasonic waves result in lower modal noise when compared to an EMAT having a single coil 12. This method results in a wave having a fixed range of wavenumbers.

FIG. 4 is a schematic view of piezoelectric fibers 21 used in defect detection systems in accordance with prior art. Collectively, the multiple piezoelectric fibers 21 represent a piezoelectric transducer 22. In operation, the individual piezoelectric fibers 21 are excited by electrodes 50, making the piezoelectric fibers 21 expand or contract, depending on the polarity of the electrodes. In the example illustrated in FIG. 4, the piezoelectric fibers 21 expand in the direction 22e when excited (energized) by the electrodes 50. For the transducer 22 with four piezoelectric elements 21, four sources of excitation (pulsers) can be used, one per each piezoelectric element 21, to generate an arbitrary sequence of excitation. With some conventional technologies, the amplitude may be varied across the transducer array elements, to achieve an effect that is equivalent to traditional phased array transduction. This conventional method is sometimes referred to as "amplitude control of guided waves."

However, for the transmitter having a large number of elements (either coils for the EMAT systems, or piezoelectric elements for piezo-based systems), a relatively large number of pulsers and their supporting electronics are required. Alternatively, a single source of excitation can be used for all transmitter elements in parallel, however, resulting in poor control of the wave direction.

Exciting the transmitter elements simultaneously by their corresponding pulsers is called a "real-time mode" of excitation. With some conventional technologies, individual transmitters (e.g., the coils 12 or piezoelectric crystals 2) of an arbitrary array are excited sequentially in time, and, after reflecting from the defect in the specimen, the reflected ultrasonic waves are also acquired sequentially off the individual receivers. The received data are filtered to select the preferred modes. The sequential excitation of the individual transmitters/receivers is called a "synthetic mode" excitation. Compared to the real-time mode excitation, the synthetic mode excitation requires less pulsers, but it also lowers the energy of the ultrasonic waves in the specimen. In many applications, especially when inspecting "lossy" substrates such as polymers, polymer coated metals or carbon fiber reinforced polymer (CFRP) structures, reducing the energy of the ultrasonic waves is generally undesirable.

Accordingly, there remains a need for defect inspection systems that can produce strong guided waves with reduced number of transmitter/receiver (transducer) elements, pulsers and/supporting electronics.

DESCRIPTION OF THE DRAWINGS

The foregoing aspects and the attendant advantages of the inventive technology will become more readily appreciated as the same become better understood by reference to the following detailed description, when taken in conjunction with the accompanying drawings, wherein:

FIGS. 5A and 5B are detail views of the embodiment shown in FIG. 5;

DETAILED DESCRIPTION

Figure 1:
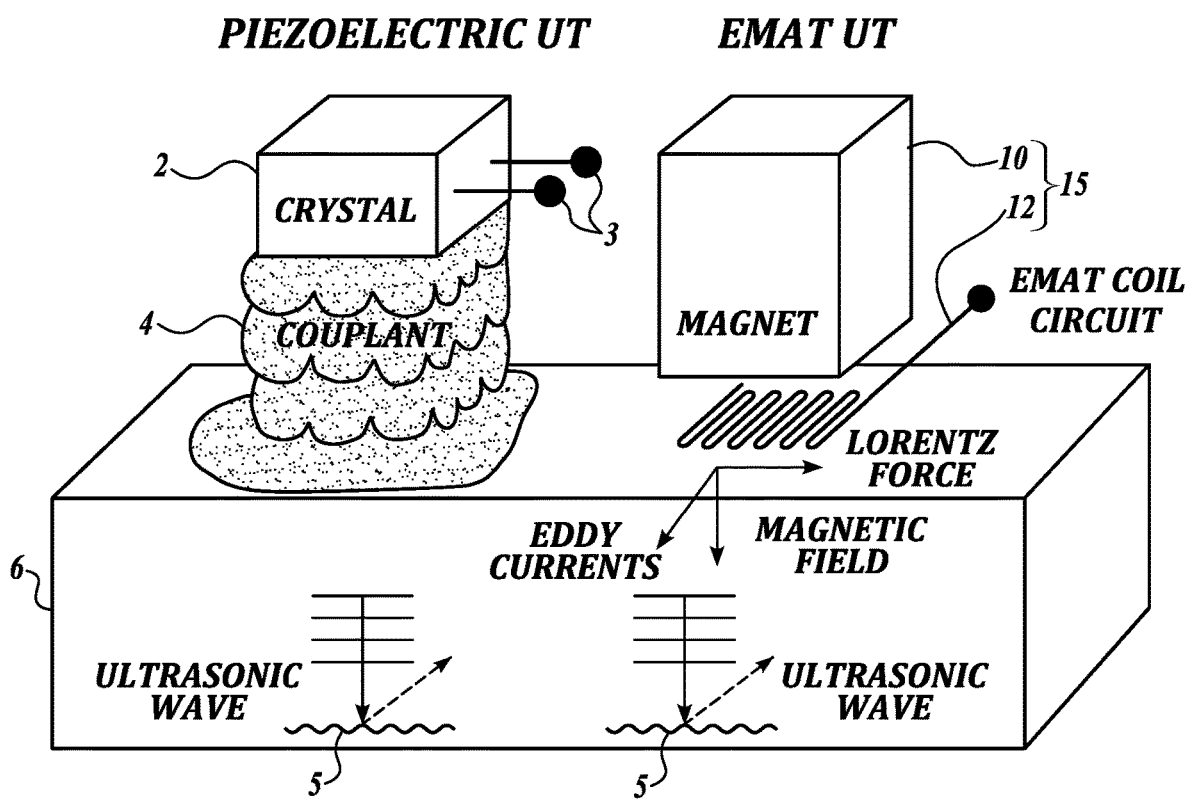
FIG. 1 is a schematic view of defect detection in accordance with prior art.
Figure 2:
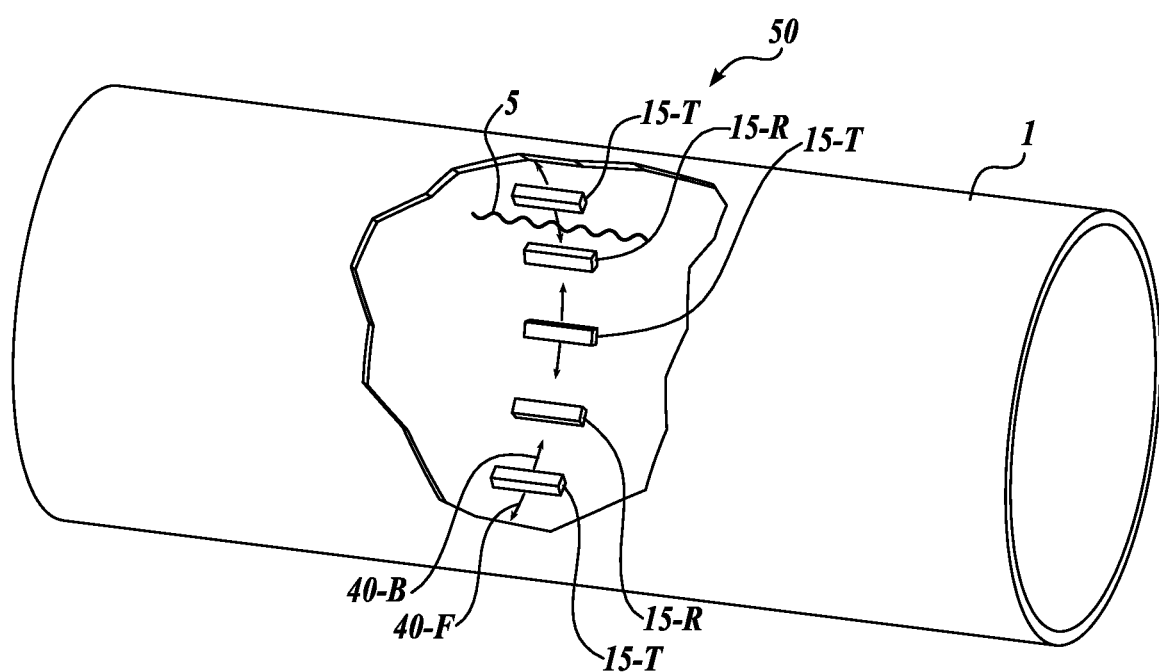
FIG. 2 is a partially schematic, isometric view of defect detection in pipes using EMATs in accordance with prior art.
Figure 3:
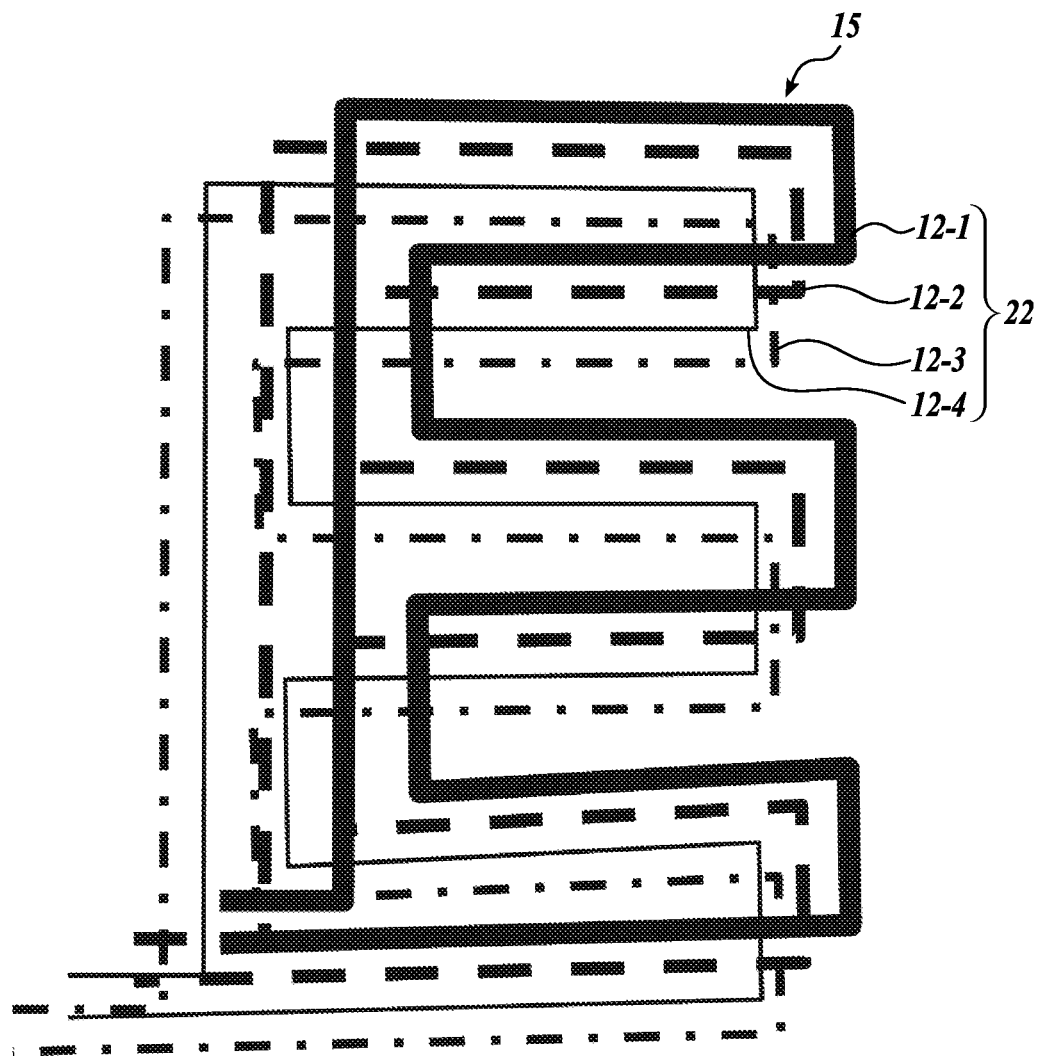
FIG. 3 is a schematic view of an EMAT with multiple coils in accordance with prior art.
Figure 4:
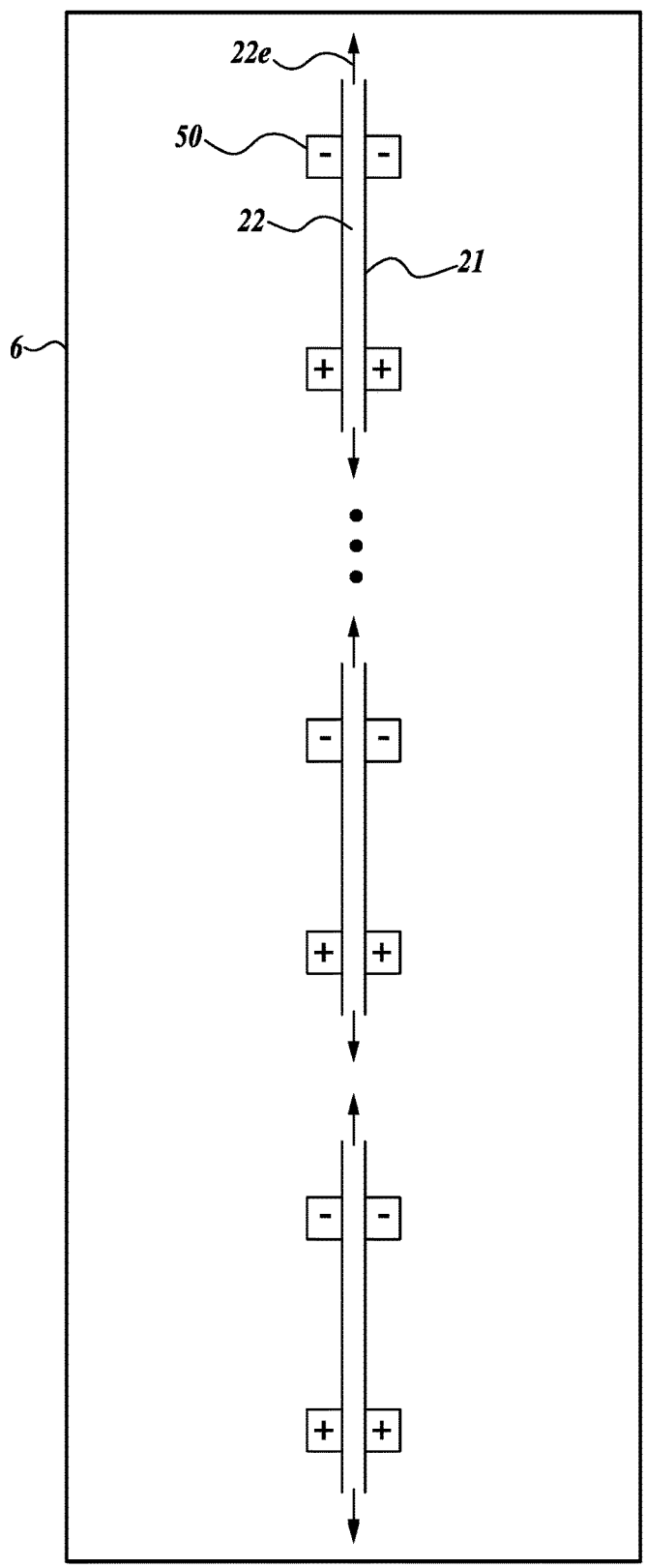
FIG. 4 is a schematic view of piezoelectric fibers used in defect detection systems in accordance with prior art.

While illustrative embodiments have been described, it will be appreciated that various changes can be made therein without departing from the spirit and scope of the inventive technology. Briefly, the inventive technology can reduce the number of ultrasonic driving channels (also referred to as "pulser ports" or "channels") when compared to conventional ultrasonic phased array systems that use the same number of elements in the transducer array. In some embodiments, the guided waves are generated over a wider range of wavelengths (analogous to a phased array transducer) when compared to conventional periodic phased array (PPA) systems (e.g. PPA shown in FIG. 3), while retaining the PPA's advantage of a reduced number of driving channels. In at least some embodiments, both bulk and guided waves may be generated with the same hardware.

In some embodiments, a switching matrix or array operates between the driving channels (pulser ports) and the transducer array to assign particular driving channels to one or more ultrasonic elements therefore reducing the number of required ultrasonic driving channels. In some embodiments, the periodicity of the phase delays and the anti-symmetric relationship between the phase delays and amplitude are exploited to reduce the number of the driving channels.

Figure 5:
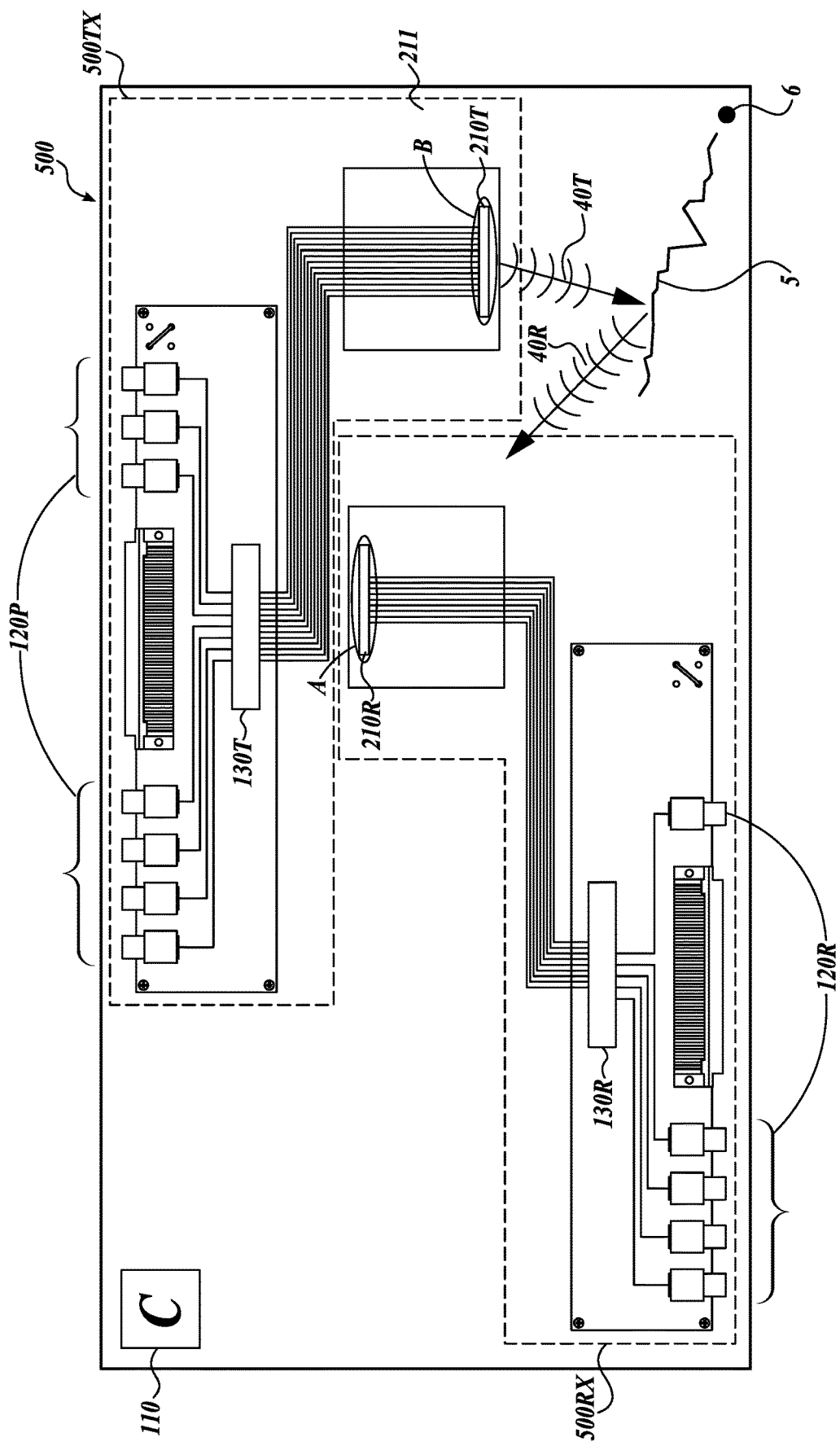
FIG. 5 is a schematic view of a defect detection system in accordance with an embodiment of the presently disclosed technology.

FIGS. 5-5B is a schematic view of a defect detection system 500 in accordance with an embodiment of the presently disclosed technology. In some embodiments, the system 500 includes a transmitter 500TX and a receiver 500RX. In operation, the ultrasound waves are generated by the transmitter 500TX, and after reflecting off a defect 5 (if any), the ultrasound waves are received by the receiver 500RX.

The illustrated transmitter 500TX includes a pulser 1201' having a set of 7 pulser ports, but embodiments with other numbers of pulser ports or only one pulser port are also possible. In some embodiments, the pulser 120P includes electrical components (e.g., power amplifiers, operational amplifiers, digital-to-analog (D/A) converters, etc.) that are sources of electrical signals (e.g., square waves or other waves).

The pulses coining from the pulser ports are routed by a switching array 130T to appropriate elements of a transmitter array 210T. The switching array 130T may include relays, transistors, diodes and/or other switching elements for connecting the pulsers/receivers with the target elements of the transmitter array 210T. In the illustrated embodiments, the switching array 130T receives input from 7 pulser ports (i.e., 7 input channels into the switching array 130T) and outputs 13 individual signals (i.e., 13 outputs out of the switching array 130T) toward the transmitter array 210T.

FIG. 5B is a detail view of the transmitter array 210T shown in FIG. 5. The transmitter array 210T includes a plurality of elements (e.g., piezoelectric elements or coils) capable of generating ultrasound into the specimen. In the context of the inventive technology, the transmitter array 210T may be termed a "metamaterial transmitter" to describe a transmitter having a sufficient number of the elements for the required resolution of the waveform received from the switching array 130T. The illustrated transmitter array 210T includes 13 individual elements connected to 13 outputs of the switching array 130T. A distance between the adjacent elements of the transceiver array is called pitch (p). In some embodiments, the transmitter array 210T may be kept in contact with the specimen 6 with a holder or coupling agent (e.g., a clamp, a metal-based glue, molasses, syrup, water etc.).

When excited, the transmitter array 210T generates ultrasound 40T into the specimen 6. In operation, the generated ultrasound may reflect from (or diffract from, or otherwise become affected by) the defect 5.

Figure 5A:
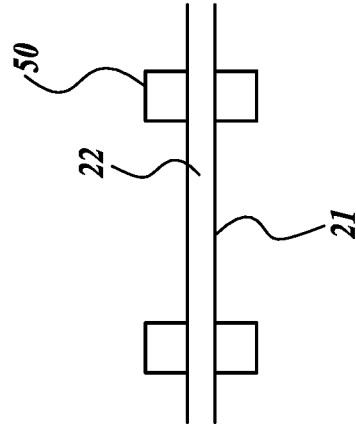
Figure 5A:
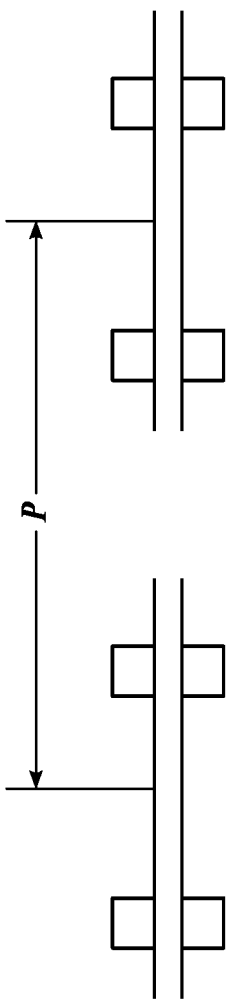

FIG. 5A is a detail view of the receiver array 210R shown in FIG. 5. In some embodiments, a receiver array 210R receives reflected ultrasound 40R. For example, the receiver array 210R may include piezoelectric fiber elements that are analogous to those of the transmitter array 210T. In presence of the ultrasound excitation, the elements of the receiver array 210R generate electrical signals that are routed to a switching array 1308. In the illustrated embodiments, the receiver array 210R includes 9 elements, but other numbers of elements are also possible. For example, the receiver array 210R may include just one receiver 210R (e.g., one piezoelectric fiber or one coil). A distance between the adjacent elements of the receiver array is called pitch (p).

In operation, the switching array 130R receives signals from the receiver array 210R, and routs the signals to the receiving ports (also referred to as "data acquiring ports") of the receiver 120R (also referred to as "data acquiring receiver"). In the illustrated array, the switching array 130R receives input from 9 individual elements of the receiver array 210R (i.e., 9 inputs into the switching array 130R) and outputs 5 individual signals (i.e., 5 output channels out of the switching array 1308) toward the receiver 120R. In some embodiments, the receivers 120R may be analog-to-digital (A/D) converters.

In some embodiments, the IX 500TX and the RX 500RX can be combined. For example, one switching array 130 may be shared by both the TX 500TX and the RX 500RX. Similarly, in at least some embodiments, one array of piezoelectric elements 210 or sensing coils may be shared by both the TX 500TX and the RX 500RX, Furthermore. the pulsers 120P and the receivers 120R may also be combined into one array by combining their electronics. In some embodiments, all the TX and RX subsystems of the defect detection system 500 are shareable, and the defect detection system 500 may be termed transceiver (TRX).

Figure 6:
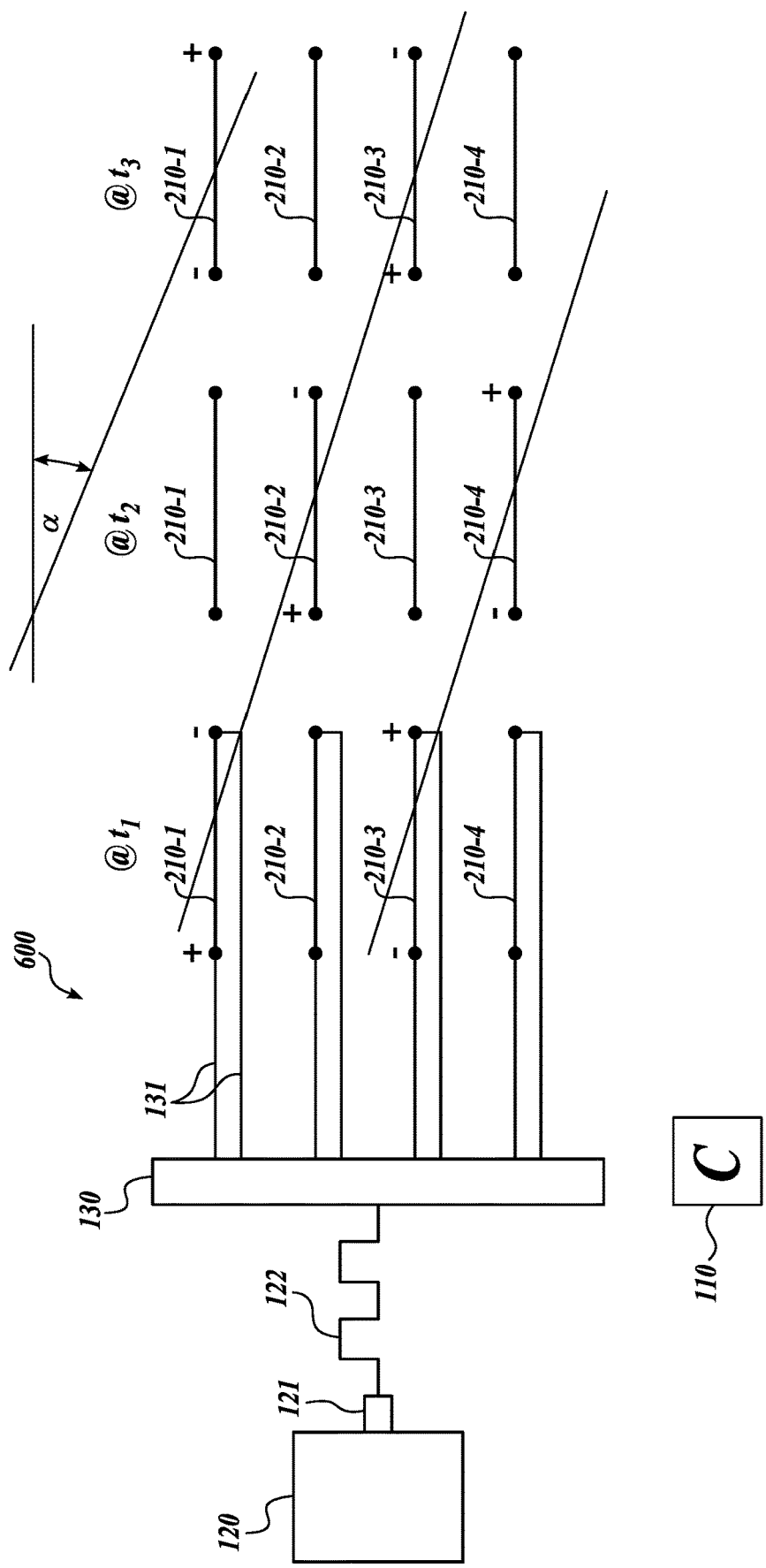
FIG. 6 is a schematic view of a quasi-real triode of operation in accordance with an embodiment of the presently disclosed technology.

FIG. 6 is a schematic view of a quasi-real time mode of operation in accordance with an embodiment of the presently disclosed technology. In operation, the pulser 120 emits electrical signal 122 at a port 121 (e.g., an electrical connector). The emitted electrical signal is also referred to as "time series" or a "channel." The switching array 130 can receive an electrical signal 122, and distribute the signal over several conducting line pairs 131 to corresponding transmitter elements 210-$i$. The illustrated transmitter ("transmitter array") 210 includes four transmitter elements 210-$i$, but other embodiments with other numbers of the transmitter elements are also possible. In some embodiments, illustrated system 600 can work as a signal receiver, or as a transceiver. For example, when the system 600 works as the receiver, the elements 210-$i$ are electrically excited (energized) by the sound waves in the specimen.

For simplicity, consider only transmission by multiple elements 210-$i$ of the transmitter array and reception by a single receiver element. To achieve a desired distribution of the time series per transmitter elements 210-$i$, the signal 122 may be phase offset and/or zeroed, and then routed to the conducting line pairs 131. In the illustrated embodiment, at time t1, transmitter element 210-1 is energized to a polarity +/−, transmitter element 210-2 is not energized, transmitter element 210-3 is energized to polarity −/+, and transmitter element 210-4 is not energized. At time t2, the voltage of the electrical signal 122 is changed, and, accordingly, the switching array 130 provides new distribution of the voltage polarities to the transmitter elements 210-$i$. Another change in the voltage polarities occurs at time t3, and so on.

In at least some embodiments, illustrated system 600 can also operate as a receiver. For example, the system 600 may include a receiver array and a single transmitter in operation, the elements 210-$i$ may receive the incoming ultrasound waves, and generate voltage in response. The voltage signals coming from the elements 210-$i$ may be routed to the receiver 120, digitized, and stored for further processing.

Some embodiments illustrated system 600 can operate as both transmitter and receiver, i.e., both the transmitter and the receiver are distinct arrays with dedicated switching arrays for each. In some embodiments, the transmitter array also acts as the receiver array and the transmitted signals and received signals are routed through the same switching array 130.

Because a subset of the array elements transmit or receive waves, there is an array action resulting in a guided wave mode selection (transmit/receive prefers a purer mode). By postprocessing the set of signals the guided waves modes may be further selected or "purified." The purification may partially occur in real-time. Therefore this method is sometimes called "quasi-real-time" method; mode of operation. During the postprocessing, time delay may be digitally applied to each seat of signals (t1, t2, t3, etc.), followed by adding/subtracting the resulting delayed signals to constructively create an effective phased array transducer.

In operation, the individual transmitter elements (e.g., piezoelectric fibers) expand/contract differently based on the polarity and intensity of their excitation voltage. In the illustrated example, the changes in the excitation of the transmitter elements 210-$i$ may result in oblique ultrasound wave fronts at angle α. Furthermore, in some instances, a suppression of oblique waves may he advantageous, which can be achieved by changing the time delays between the pulsers (e.g., real-time mode of operation) or at post-processing of the acquired signal (e.g., quasi-real time mode of operation).

In at least some embodiments, illustrated system 600 can also operate as a receiver. For instance, the elements 210-$i$ may receive the incoming ultrasound waves, and generate voltage in response. The voltage signals coining from the elements 210-$i$ may be routed to the receiver 120, digitized, and stored for further processing.

Figure 7:
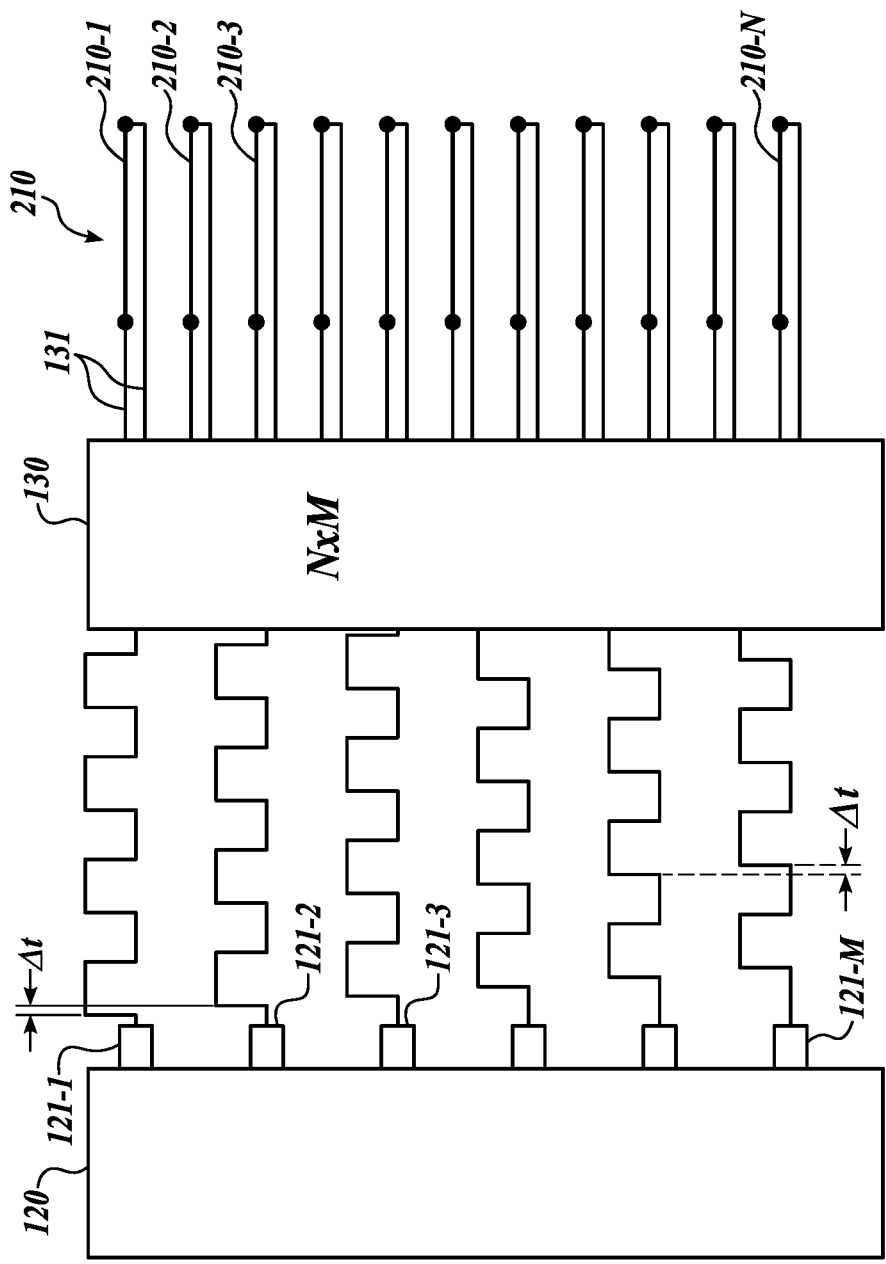
FIG. 7 is a schematic view of a real-time mode of operation in accordance with an embodiment of the presently disclosed technology.

FIG. 7 is a schematic view of a real-time mode of operation in accordance with an embodiment of the presently disclosed technology. With the illustrated mode of operation, the individual transducer elements 210-$i$ are energized simultaneously. The operation of such a transducer is termed "real-time" mode of operation. In some embodiments, the number of the individual transducer elements 210-$i$ (N) may be larger than the number of pulser ports 121-$i$ (M).

In operation, the pulser ports (channels) 121-$i$ provide electrical signals, for example, square waves at required frequency and voltage (amplitude). These square waves at the pulser ports 121-$i$ may he sequentially offset by, for example, a constant Δt to produce ultrasonic waves at desired angle. In other embodiments, the time offsets Δt among the electrical signals can be variable. In some embodiments, a signal (e.g., a square wave signal) generated by a pulser may be provided as, for example, unchanged signal to one transducer element 210-$i$, and as an inverted signal to another transducer element 210-$i$, and/or a phase delayed signal at different transducer elements 210-$i$.

FIGS. 8-11 are schematic views of wavelength patterning in accordance with embodiments of the presently disclosed technology. For brevity and conciseness, the embodiments are described in view of the elements of the transmitter (TX) array 210T, but equivalent embodiments are also possible for the elements of the receiver (RX) array 210R. Stated differently, the array 210 may operate as either the TX or RX, that is the array 210 may operate as a transceiver (TRX).

Figure 8:
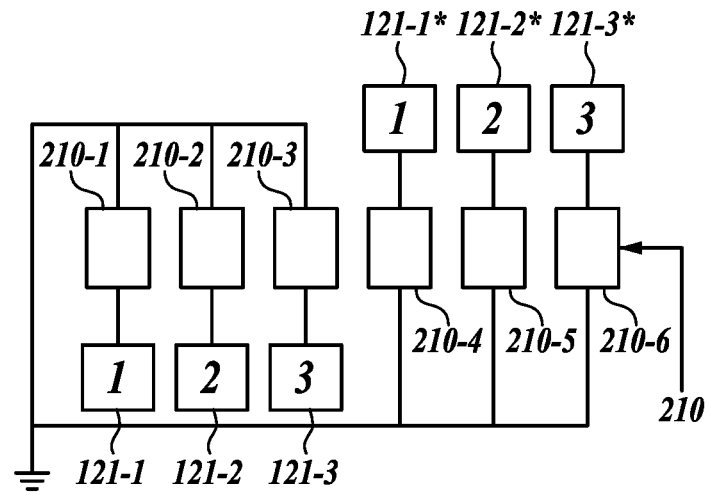
FIGS. 8-11 are schematic views of wavelength patterning in accordance with embodiments of the presently disclosed technology.

FIG. 8 illustrates an ultrasonic waveform generated by a 3-port pulser over a 6-element transducer 210. In operation, the signals from the pulser 120 are routed through the switching array 130 to the individual elements of the transducer 210. However, for brevity and simplicity, the switching array 130 is not shown in the schematical representations of FIGS. 8-11.

In the illustrated embodiment, the pulser ports 121-1, 121-2 and 121-3 provide electrical signals 122 to the elements 210-1, 210-2 and 210-3, respectively. Furthermore, the switching array 130 (not shown) may invert (or cause a 180 degree phase-offset) signals from the pulser ports 121-1 to 121-3 to generate inverted or phase-offset signals (denoted with "*") to the transducer elements 210-4 to 210-6. For example, the transducer elements 210-1-210-3 may be excited to "high," while the transducer elements 210-3-210-6 may be excited to "low," resulting in a square-wave-like excitation over the six transducer elements 210-1-210-6. As a result, three pulser ports 121-*i* may drive six elements 210-*i* of the transducer array while operating in the real-time mode of operation.

In some embodiments, the pulser may operate with a single pulser port 121 using the time delays (as explained with reference to FIG. 6 above). Such pulser operates in the quazi-real-time mode of operation.

Figure 9:
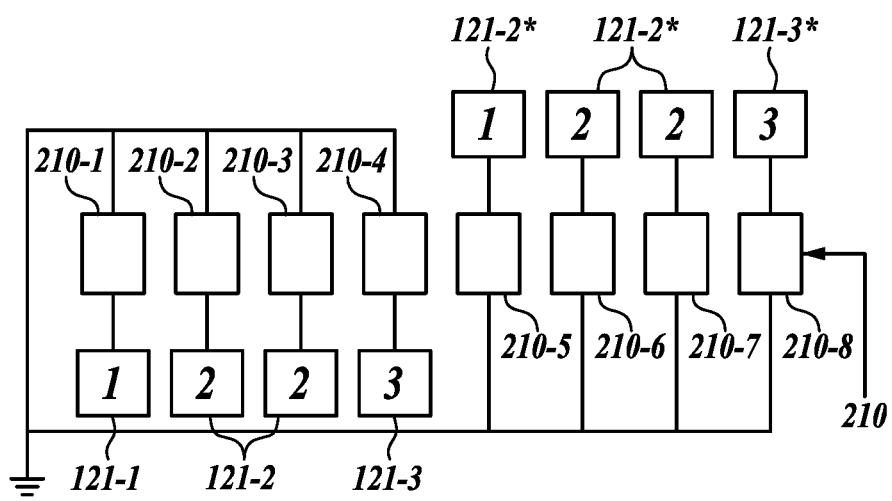
Figure 10:
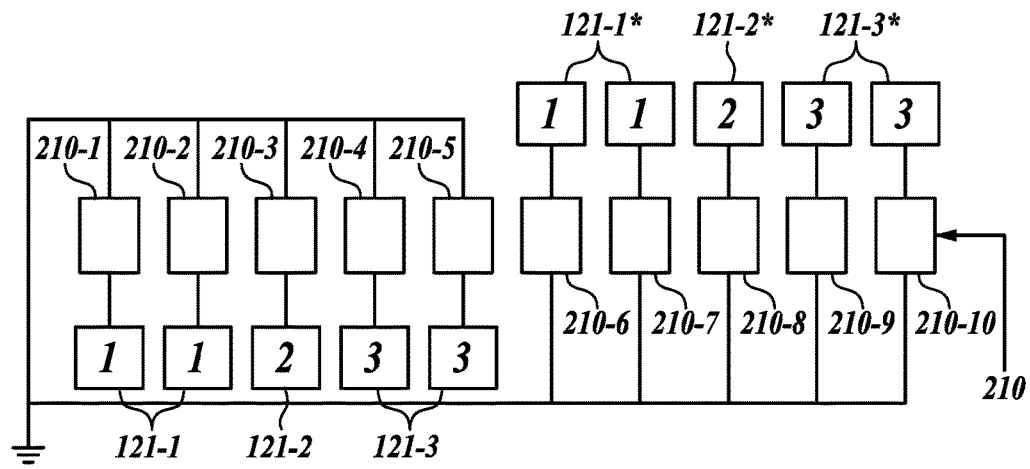
Figure 11:
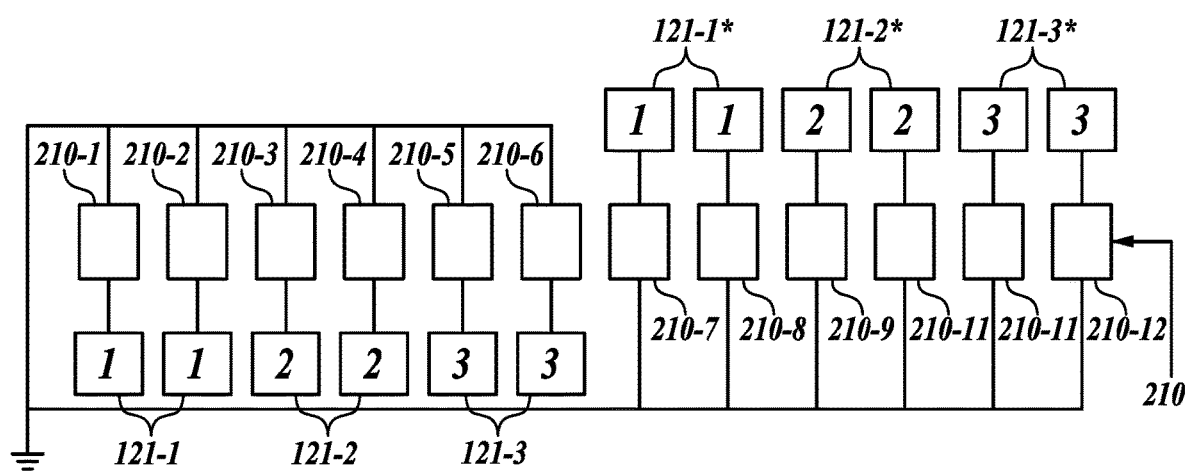

FIG. 9 illustrates an ultrasonic waveform generated by a 3-port pulser over an 8-element transducer 210. In the illustrated embodiment, the pulser port 121-1 excites the transducer element 210-1, and the inverted or phase offset signal from the pulser port 121-1 excites the transducer element 210-5. Furthermore, the pulser port 121-2 excites two transducer elements 210-2 and 210-3, and the inverted or phase offset signal from the pulser port 121-2 excites the transducer elements 210-6 and 210-7. The pulser port 121-3 excites the transducer element 210-4, and the inverted or phase offset signal from the pulser port 121-3 excites the transducer element 210-8. As a result, a square-wave-like excitation may be achievable with the 3-port pulser over the 8-element transducer array. FIGS. 10 and 11 illustrate ultrasonic waveforms generated by a 3-port pulser over a 10-element transducer and a 12-element transducer, respectively. In both cases, the ultrasonic waveform is achieved with the pulser 120 having a smaller number of ports 121 than the number of elements in the transducer array 210.

Some possible distributions (patterns) of the excitation of the individual elements of the transducer array by a 3-port (3-channel) pulser are illustrated in Table 1 below. The term "half-wavelength" describes the excitation waveform over one half of the transducer elements 210-*i* in the transducer array 210.

TABLE 1

Excitation of transducer array with 3 pulser ports (channels)

| | Channel No. | | | No. of elements per | No. of elements in |
|---|---|---|---|---|---|
| | 1 | 2 | 3 | half-wavelength | transducer array |
| Distribution | 1 | 1 | 1 | 3 | 6 |
| Pattern | 1 | 2 | 1 | 4 | 8 |
| (how | 2 | 1 | 2 | 5 | 10 |
| many | 2 | 2 | 2 | 6 | 12 |
| elements | 2 | 3 | 2 | 7 | 14 |
| per | 3 | 2 | 3 | 8 | 16 |

TABLE 1-continued

Excitation of transducer array with 3 pulser ports (channels)

| | Channel No. | | | No. of elements per | No. of elements in |
|---|---|---|---|---|---|
| | 1 | 2 | 3 | half-wavelength | transducer array |
| channel) | 3 | 3 | 3 | 9 | 18 |
| | 3 | 4 | 3 | 10 | 20 |
| | 4 | 3 | 4 | 11 | 22 |

In different embodiments, other possible distributions (patterns) of the excitation of the individual elements of the transducer array are also possible. For example, some possible distributions (patterns) of the excitation of the individual elements of the transducer array by a 5-port (5-channel) pulser and a 7-port (7-channel) pulser are illustrated in Tables 2 and 3, respectively.

TABLE 2

Excitation of transducer array with 5 pulser ports (channels)

| | Channel No. | | | | | No. of elements per | No. of elements in |
|---|---|---|---|---|---|---|---|
| | 1 | 2 | 3 | 4 | 5 | half-wavelength | transducer array |
| Distribution | 1 | 1 | 1 | 1 | 1 | 5 | 10 |
| Pattern | 1 | 1 | 2 | 1 | 1 | 6 | 12 |
| (how | 1 | 2 | 1 | 2 | 1 | 7 | 14 |
| many | 1 | 2 | 2 | 2 | 1 | 8 | 16 |
| elements | 2 | 2 | 1 | 2 | 2 | 9 | 18 |
| per | 2 | 2 | 2 | 2 | 2 | 10 | 20 |
| channel) | 2 | 2 | 3 | 2 | 2 | 11 | 22 |

TABLE 3

Excitation of transducer array with 7 pulser ports (channels)

| | Channel No. | | | | | | | No. of elements per | No. of elements in |
|---|---|---|---|---|---|---|---|---|---|
| | 1 | 2 | 3 | 4 | 5 | 6 | 7 | half-wavelength | transducer array |
| Distribution | 1 | 1 | 1 | 1 | 1 | 1 | 1 | 7 | 14 |
| Pattern | 1 | 1 | 1 | 2 | 1 | 1 | 1 | 8 | 16 |
| (how | 1 | 1 | 2 | 1 | 2 | 1 | 1 | 9 | 18 |
| many | 1 | 1 | 2 | 2 | 2 | 1 | 1 | 10 | 20 |
| elements | 1 | 2 | 2 | 1 | 2 | 2 | 1 | 11 | 22 |
| per | | | | | | | | | |
| channel) | | | | | | | | | |

Figure 12:
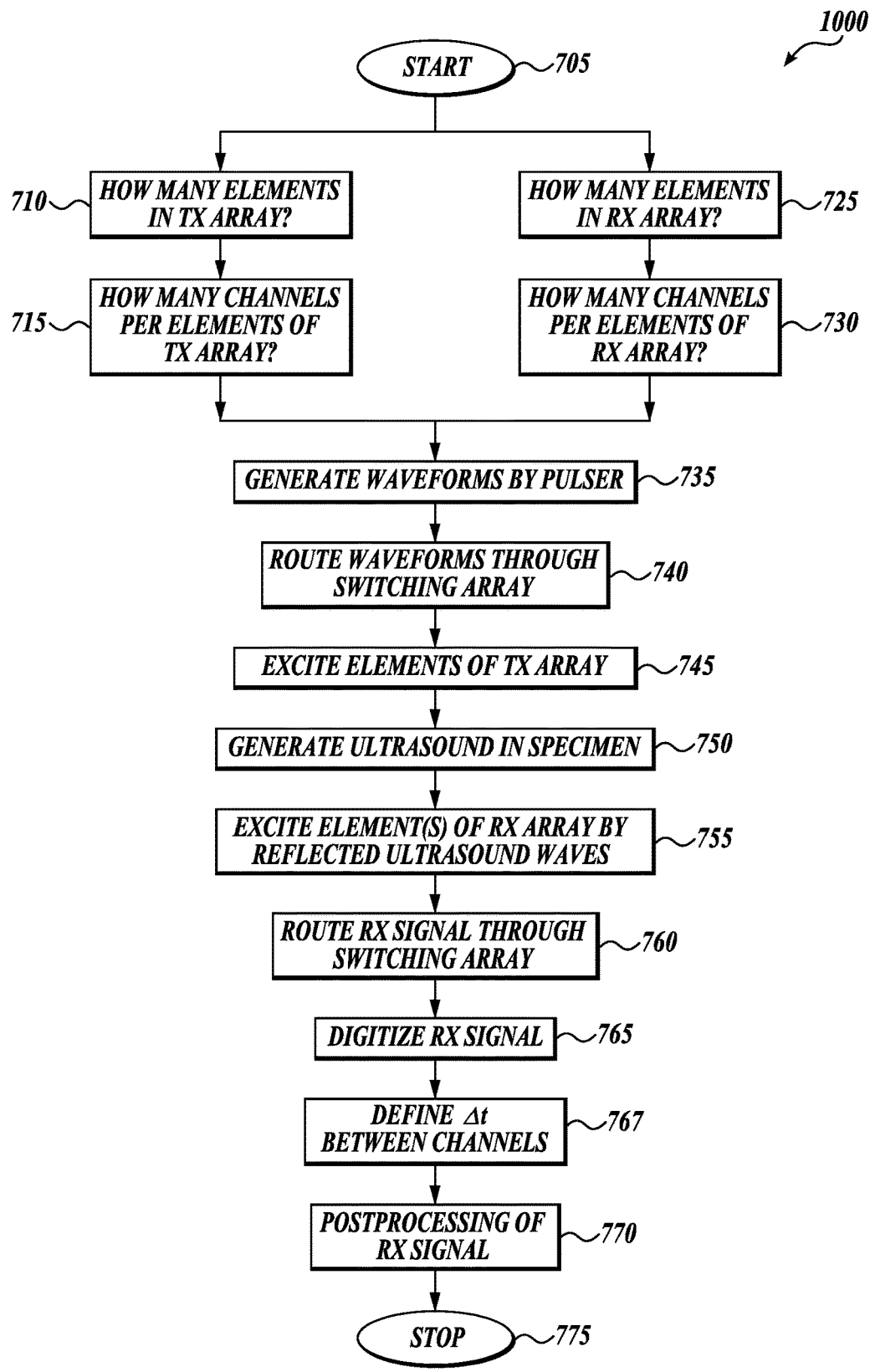
FIG. 12 is a flow diagram of a quasi-real-time method of operation in accordance with embodiments of the present technology.

FIG. 12 is a flow diagram 1000 of a quasi-real-time method of operation in accordance with embodiments of the present technology. In the described method, the pulser 120 operates with one pulser port 121. An embodiment of such a pulser in operation is described with reference to FIG. 6. In some embodiments, the method may include additional steps or may be practiced without all steps illustrated in the flow chart.

The method may start at step 705, and proceed to step 710. In step 710, a determination is made about the size of the transmitter (TX) array. In particular, the number of the individual elements (e.g., piezoelectric fibers) in the transmitter array is determined. The transmitter array may be termed a metamaterial transmitter when including a sufficient number of the individual elements for resolving the wavefront received from the switching array, which, in turn, results in transmission or reception of the purer guided wave modes.

In step 715, the number of channels is determined. The signal transmitted by the pulser port 121 may be appropriately time offset and distributed over the individual transmitter elements 210-*i* in the transmitter array 210. For example, the signal transmitted by the pulser port 121 may be divided into 4 channels distributed over 7 transmitter elements of one-half of the transmitter array 210. The 4 channels may be appropriately phase offset or inverted for the distribution over the other 7 transmitter elements of the second one-half of the transmitter array 210.

Conversely, in steps 725 and 730, the number of elements in the RX array and the channel distribution per the elements of the RX array are determined.

In step 735, the waveform is generated by the pulser 120 having a single pulser port 121. In some embodiment, the waveform can be a square wave waveform.

In step 740, the generated waveform is routed through the switching array. In some embodiments, the switching array applies phase offsets, zeroing, and/or signal inversion to achieve the required waveform at the output of the switching array.

In step 745, the individual elements of the TX array are excited with the waveforms coming from the switching array. This excitation, in turn, generates ultrasound waves in the specimen in step 750.

In step 755, the elements of the RX array are excited by reflected ultrasound waves. In at least some embodiments, the ultrasound waves reflect from the defects and/or imperfections in the specimen. In some embodiments, the RX and TX array may physically be the same, and may operate at different times as the TX array and the RX array (e.g., operating in time domain division). Accordingly, in some embodiments the array 210 may be the transceiver (TRX) array.

In step 760, the signal generated by the reflected ultrasound wave impinging on the RX array is routed through the switching array. In step 765, the RX signal is received by the receiver 120R, and digitized using, for example, A/D converters.

In step 7767, a determination is made about the time offset Δt between the individual signals acquired by the transducer elements. In some embodiments, a suppression of unwanted waves may be improved by changing the time offsets (delays) Δt between the acquired signals while post-processing the acquired signal in quasi-real time mode of operation.

In step 770, the RX signal is post-processed to determine, for example, location of the defect, severity of the defect, etc. The post-processing of the RX signal may be executed on general or special purpose computers or controllers. The system ends in step 775.

Figure 13:
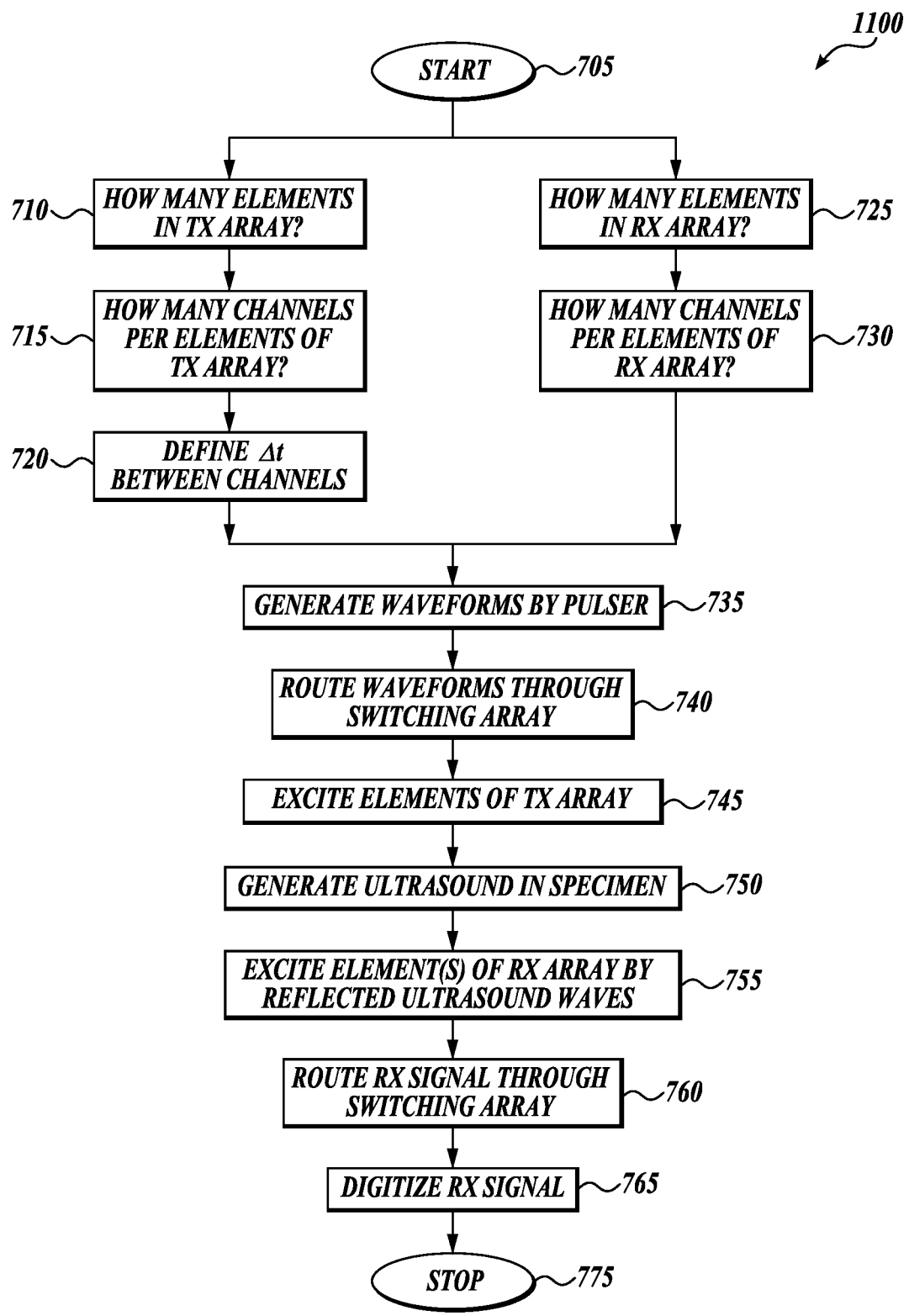
FIG. 13 is a flow diagram of a real-time method of operation in accordance with embodiments of the present technology.

FIG. 13 is a flow diagram 1100 of a real-time method of operation in accordance with embodiments of the present technology. In the described method, the pulser 120 includes multiple pulser ports 121 that operate simultaneously. An embodiment of such a pulser in operation is described with reference to FIG. 7. In general, the number of individual elements 2104 may exceed the number of the pulser ports 1204. Therefore, determinations of the number of TX/RX elements per individual channels may still be needed (steps 715 and 730). In step 720, a determination is made about the time offset Δt between the individual channels generated by the pulser ports 121-*i*.

Figure 14:
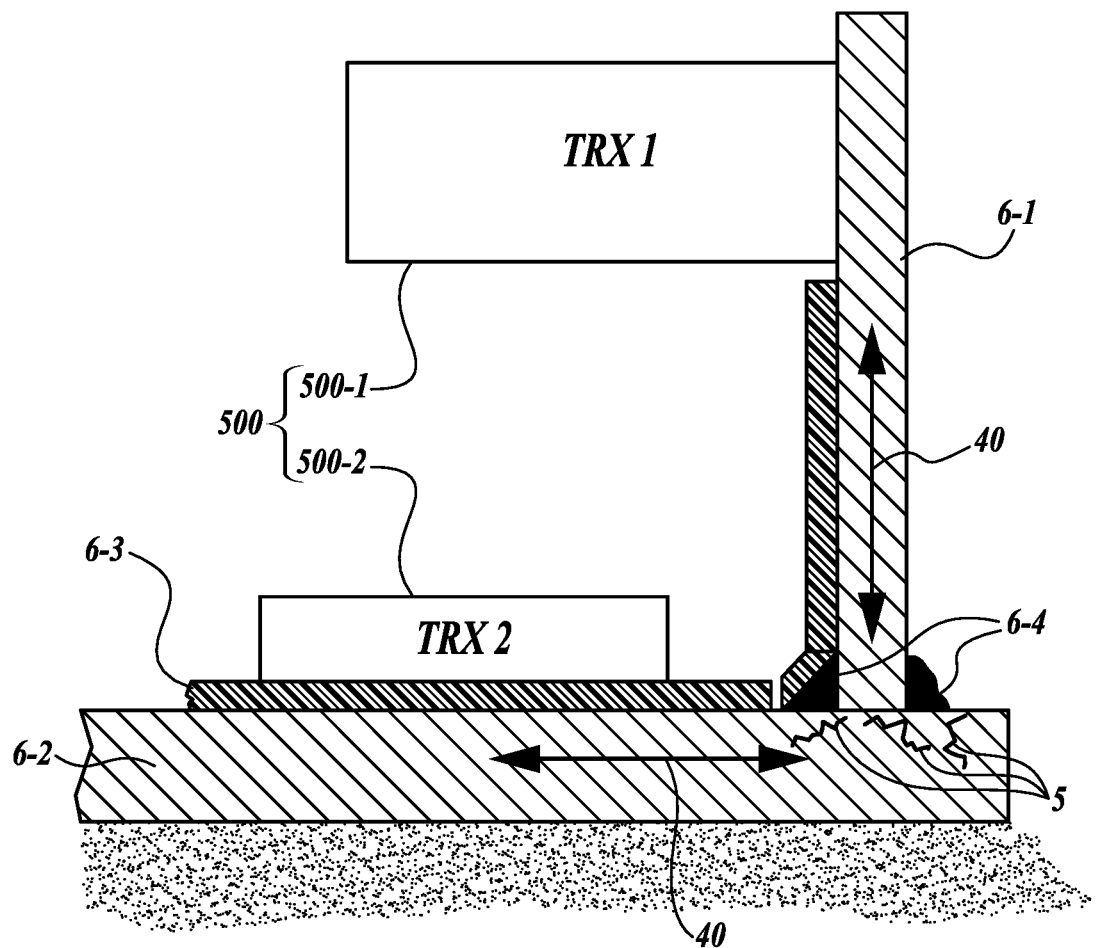
FIG. 14 is a schematic view of a defect detection system in accordance with an embodiment of the presently disclosed technology.

FIG. 14 is a schematic view of a defect detection system in accordance with an embodiment of the presently disclosed technology. In some embodiments, the specimen under test may be a segment of a vessel or a tank. For example, the specimen may include a vertical wall 6-1 that is attached to a horizontal wall 6-2 by welds 6-4. In many situations, the defects 5 tend to develop in the vicinity of the welds 6-4. The vessel/tank may also include a protective liner 6-3.

In some embodiments, the defect detection system 500 includes a transceiver (TRX) 500-1 positioned along the vertical wall 6-1 and a TRX 500-2 positioned along the horizontal wall 6-2. In operation, the TRX-es 500-1, 500-2 may transmit/receive ultrasound waves 40 along the horizontal wall 6-2 and the vertical wall 6-1. For example, the TX of the TRX 500-1 may transmit ultrasound waves 40 into the vertical wall 6-1. Ultrasound waves 40 may reflect (or diffract) off the defects 5 toward the RX of the TRX 500-2 that is excited by the reflected ultrasound waves. In other embodiments, different combinations of the functionalities of the TRX-es 500-1 and 500-2 are possible.

Lumping of Elements and Weighting of Signals

The description of the lumping is based on a following sample configuration, but other system configurations are also possible. The described system includes a pulser having 3-ports (also referred to "3 channels"). The ports/channels are distributed across a transducer array having 4 elements per half wavelength. Of these 4 elements, the first driving pulser port/channel is connected to the first element of the transducer; the second pulser port/channel is connected to the second and third elements; and the third pulser port/channel is connected to the $4^{th}$ element. This distribution corresponds to the sequence "1, 2, 1" in Table 1 (the second row of the "Distribution Pattern" in Table 1) where the second driving channel is connected to two elements of the transducer array. Consequently, these two elements (the elements 2 and 3) act as a single lumped element.

Since the spectral characteristics of the lumped element are different from those of an individual element, an amplitude correction may be necessary. The amplitude correction may be calculated using the spatio-temporal filter approach. A possible spatio-temporal model for the transducer array is as follows:

$$f(x, t) = h(x)g(t) + h(x-p)g(t-\Delta T_1) + h(x-2p)g(t-\Delta T_1) + h(x-3p)g(t-\Delta T_2) \quad \text{Eq. (1)}$$

where h(x) represents the geometry of an element of the transducer array; g(t) is the time domain function; p is the pitch of transducer array and; and $\Delta T_1$ and $\Delta T_2$ are the time delays that should be determined.

The two-dimensional Fourier transform of Equation 1 is given by, $$F(k, \omega) = H(k)G(\omega) \begin{bmatrix} 1 + \exp\{i(1.5\ kp - \omega\Delta T_1)\} \\ \{\exp(-i0.5\ kp) + \exp(i0.5\ kp)\} + \\ \exp\{3\ kp - \omega\Delta T_1)\} \end{bmatrix} \quad \text{Eq. (2)}$$

where k and w are the wavenumber and the angular frequency, respectively. Simplifying Equation 2, the following may be written:

$$F(k, \omega) = H(k)G(\omega) \begin{bmatrix} 1 + \exp\{i(1.5\ kp - \omega\Delta T_1)\}2\cos(0.5\ kp) + \\ \exp\{3\ kp - \omega\Delta T_1)\} \end{bmatrix} \quad \text{Eq. (3)}$$

Observing the second term of the summation in Equation 3, an amplitude correction is given by:

$$A = 2\sec(0.5\ kp) \quad \text{Eq. (4a)}$$

The time delays may be calculated using the following formulae:

$$\Delta T_1 = [(1.5\ kp)\%(2\pi)]/\omega \qquad \text{Eq. (4b)}$$

$$\Delta T_2 = (3\ kp)\%(2\pi)]/\omega \qquad \text{Eq. (4c)}$$

where "%" is the modulus operator (reminder after division)

Equation 4a shows that the amplitude corrections can be calculated using the knowledge of the number of elements being excited by a given channel (pulser port). The required time delays may be calculated using the effective position of the elements. When only one element is connected to each individual channel, the amplitude correction may not be necessary.

Sample Results

Figure 15:
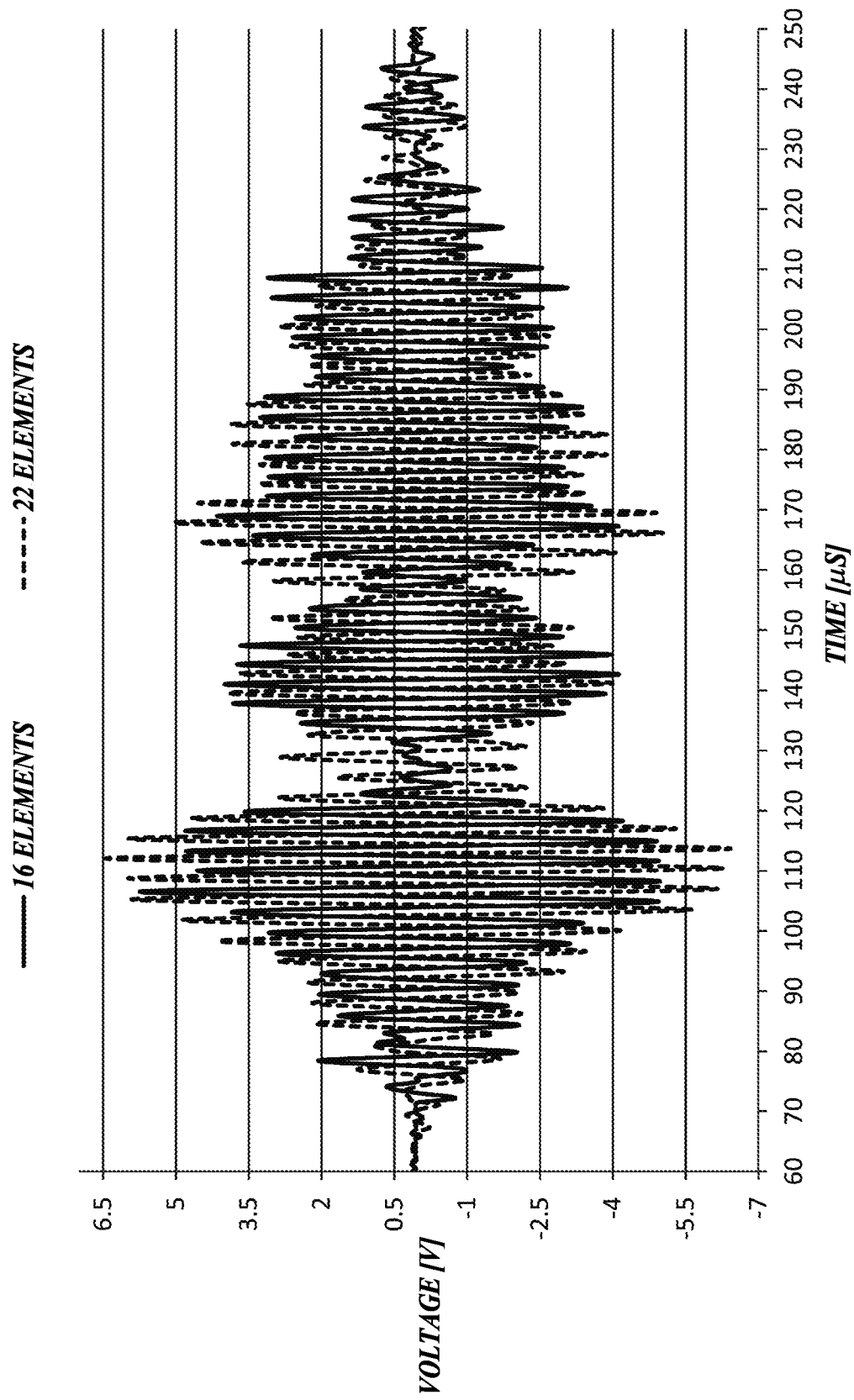
FIG. 15 is a graph of ultrasonic waves generated in accordance with embodiments of the present technology.

FIG. 15 is a graph of ultrasonic waves generated in accordance with embodiments of the present technology. The horizontal axis represents time in microseconds. The vertical axis represents the strength of the received signal in Volts.

The solid line represents the ultrasound wave generated using the conventional technology where a pulser having 16 pulser ports drives a TX having 16 individual elements. The highest power peaks for the transmitted signal are about +/−5.4 Volts.

The dashed line represents the ultrasound wave generated using an embodiment of the present technology where a pulser having 7 pulser ports drives a TX having 22 individual elements. Such a distribution of pulser ports per individual elements of the TX array is shown in the last row of Table 3, but other distributions are also possible. For the illustrated embodiment, the highest power peaks for the transmitted signal are about +/−6.5 Volts. Therefore, with at least some embodiments of the inventive technology, the signal strength is increased even though the number of the pulser ports/channels (i.e., 7) is decreased in comparison to the number of the pulser ports/channels used with the conventional technology (i.e., 16). The modal content of both the cases also appears to be similar.

Various Applications

Steering of Guided Waves

The inventive technology can also be adapted to steering of guided waves. For example, steering of guided waves can be achieved using at least a one-dimensional array of transducers. Improved steering of the guided wave can also be achieved using a two dimensional array of transducers.

Amplitude Control of Guided Waves

In some embodiments, the amplitude of the signal at the individual transducer elements may be controlled. Furthermore, apodization (e.g., Hann window) may be used to reduce the spurious wave numbers or wave directions. Amplitude variations for such transducers also follow patterns of periodicity and anti-symmetry analogous to that of the phased array transducers. The amplitude control may substitute time delay.

Application to EMATs

As explained above, the inventive technology may include EMATs of various types. However, EMATs typically involve high currents and the switching matrix should be able to handle high currents for the apparatus to properly function. For example, the switching array may use low density pattern of switches where each switch is electrically well isolated from the other. Such switching matrix may also be used with high intensity ultrasound generation by piezoelectric array of transducers when the individual elements require relatively high voltages.

Application to Bulk Waves

Steering of bulk ultrasonic waves may also be improved using this approach. For example, the electro-acoustic conversion efficiency improves when the inventive technology is applied to a transducer array with a large number of elements for both bulk and guided ultrasonic waves.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

We claim:

1. An apparatus for inspecting a solid object using ultrasound, comprising:
    a pulser having a plurality of pulser ports configured to output electrical signals;
    a switching array configured to:
        receive the signals from the pulser ports as individual channels, and
        route the signals to individual elements of a transmitter array; and
    the transmitter array, wherein each element of the transmitter array is configured to generate ultrasound in the solid object in response to the signal received from the switching array,
    wherein at least two elements of the transmitter array are configured to receive the signals from different pulser ports, and wherein at least two elements of the transmitter array are configured to receive the signals from the same pulser port.

2. The apparatus of claim 1, wherein the individual elements of the transmitter array comprise piezoelectric fibers.

3. The apparatus of claim 1, wherein the individual elements of the transmitter array comprise coils.

4. The apparatus of claim 1, wherein the switching array is a transmitter switching array, and the signals are transmitter signals, the apparatus further comprising:

a receiver array, wherein each element of the receiver array is configured to generate electrical receiver signals in response to ultrasound waves; and a receiver switching array configured to:
receive the receiver signals from the elements of the receiver array, and
route the receiver signals to individual receiver ports of a receiver.

5. The apparatus of claim 4, wherein the transmitter array and the receiver array have different numbers of elements.

6. The apparatus of claim 4, wherein the transmitter array and the receiver array are the same array.

7. The apparatus of claim 1, wherein the transmitter array is operable over a range of frequencies.

8. The apparatus of claim 1, wherein the transmitter array is operable over a range of voltages.

9. The apparatus of claim 1, wherein the transmitter array comprises an even number of individual elements, and wherein one half to the individual elements is configured to receive the signals that are inverted, zeroed or phase-offset with respect the signals received by other half the individual elements.

10. The apparatus of claim 1, wherein the at least two elements of the transmitter array that are configured to receive the signals from the same pulser port receive the signals having same amplitude.

11. The apparatus of claim 1, wherein the at least two elements of the transmitter array that are configured to receive the signals from the same pulser port comprise a lumped element.

12. The apparatus of claim 11, wherein the individual elements of the lumped element are excited using time delays ΔT1 and ΔT2, and wherein:

$$\Delta T1 = [(1.5 \text{ kp})\%(2\pi)]/\omega$$

$$\Delta T2 = (3 \text{ kp})\%(2\pi)/\omega$$

where k is a wavenumber, p is a pitch of the transmitter array, ω is an angular frequency "%" is a modulus operator.

13. An apparatus for inspecting a solid object using ultrasound, comprising:
a pulser having a plurality of pulser ports configured to output electrical signals;
a switching array configured to:
receive the signals from the pulser ports as individual channels, and
route the signals to individual elements of a transmitter array; and
the transmitter array, wherein each element of the transmitter array is configured to generate ultrasound in the solid object in response to the signal received from the switching array,
wherein at least two elements of the transmitter array are configured to receive the signals from different pulser ports, and wherein a number of the pulser ports is smaller than a number of elements in the transmitter array.

14. The apparatus of claim 13, wherein the switching array is a transmitter switching array, and the signals are transmitter signals, the apparatus further comprising:
a receiver array, wherein each element of the receiver array is configured to generate electrical receiver signals in response to ultrasound waves; and
a receiver switching array configured to:
receive the receiver signals from the elements of the receiver array, and
route the receiver signals to individual receiver ports of a receiver.

15. The apparatus of claim 14, wherein the transmitter array and the receiver array have different numbers of elements.

16. The apparatus of claim 14, wherein the transmitter array and the receiver array are the same array.

17. A method for inspecting solid objects, comprising:
sending electrical signals from pulser ports of a pulser;
receiving the signals by M inputs of a switching array;
routing the signals to N outputs of the switching array, wherein N is greater than M;
receiving the signals from the switching array by individual elements of a transmitter array, wherein at least two elements of the transmitter array are configured to receive the signals from different pulser ports, and wherein at least two elements of the transmitter array are configured to receive the signals from the same pulser port; and
in response to the received signals, generating ultrasound in the solid object by the elements of the transmitter.

18. The method of claim 17, further comprising:
applying a time delay to the signals; and
applying an amplitude correction to the signals.

19. The method of claim 17, wherein the switching array is a transmitter switching array, and the signals are transmitter signals, the method further comprising:
receiving ultrasound waves by individual elements of a receiver array;
in response to received ultrasound waves, generating receiver electrical signals by the individual elements of the receiver;
receiving the receiver signals by the elements of the receiver array, and routing the receiver signals to individual receiver ports of a receiver.

20. The method of claim 19, wherein the transmitter array and the receiver array have different number of elements.

21. The method of claim 19, wherein the transmitter array and the receiver array are the same array.

22. The method of claim 17, further comprising performing an analog to digital (A/D) conversion of the receiver signals.

23. The method of claim 17, further comprising determining an amplitude correction factor the at least two elements of the transmitter array that are configured to receive the signals from the same pulser port.

24. A method for inspecting solid objects, comprising:
sending electrical signals from a pulser port of a pulser;
receiving the signals by inputs of a switching array;
routing the signals to a plurality of outputs of the switching array, wherein the signals at the outputs of the switching array are mutually time-offset;
receiving the signals from the switching array by individual elements of a transmitter array; and
in response to the received signals, generating ultrasound in the solid object by the elements of the transmitter.

25. The method of claim 24, further comprising:
applying a time delay to the signals; and
applying an amplitude correction to the signals.

26. The method of claim 24, further comprising zeroing at least some signals at the outputs of the switching array.

27. The method of claim 24, further comprising inverting at least some signals at the outputs of the switching array.

* * * * *